United States Patent [19]

Vogeley

[11] 4,081,623
[45] Mar. 28, 1978

[54] SIGHT OPERATED TELEPHONE AND MACHINE CONTROLLER

[75] Inventor: Arthur W. Vogeley, Yorktown, Va.

[73] Assignee: Bio-Systems Research, Inc., Yorktown, Va.

[21] Appl. No.: 742,106

[22] Filed: Nov. 15, 1976

[51] Int. Cl.² .............................................. H04M 1/26
[52] U.S. Cl. ......................... 179/90 BD; 179/90 AN; 250/221; 340/190
[58] Field of Search ................ 179/2 A, 2 DP, 1 HF, 179/18 B, 90 BD, 90 CS, 84 L; 200/61.02; 340/148, 165, 189 R, 189 M, 190, 201 R, 201 P, 332, 366 B, 382; 250/215, 221, 222

[56] References Cited

U.S. PATENT DOCUMENTS

| Re. 27,728 | 8/1973 | Kosker et al. | 340/190 |
| 3,379,885 | 4/1968 | Nork | 250/221 |
| 3,736,410 | 5/1973 | Ragland et al. | 179/90 CS |
| 3,804,496 | 4/1974 | Crane et al. | 250/221 |
| 3,806,725 | 4/1974 | Leitz | 250/221 |
| 3,851,328 | 11/1974 | Sottile et al. | 250/221 |
| 3,986,030 | 10/1976 | Teltscher | 250/215 |

*Primary Examiner*—Kathleen H. Claffy
*Assistant Examiner*—Gerald L. Briganoe
*Attorney, Agent, or Firm*—Martin Fruitman

[57] ABSTRACT

A machine and telephone controller for complex machine functions which is operated by simply looking at it and winking the eye in a preset code. Photocell and electronic logic circuitry stop a sequencing digital display at the desired numerals and activates the machine or telephone for the displayed number which may indicate either a function of a machine or a telephone number to be dialed.

11 Claims, 2 Drawing Figures

SIGHT OPERATED TELEPHONE AND MACHINE CONTROLLER

BACKGROUND OF THE INVENTION

The invention relates generally to machine control and more specifically to an apparatus for remote control of complex machines by interaction with the human eye.

Remote control by human action has generally involved either wire, radio or sonic links between the operator and machine. But these links have traditionally been activated by conventional operator actions such as pushing buttons or turning selection knobs. Such physical actions, while satisfactory for the vast majority of situations, do not fulfill the requirements of all situations. Handicapped persons, for instance, frequently cannot perform the same mechanical operations as others and are therefore highly restricted in the machines they can control. Yet many handicapped individuals lead active and productive lives when equipment is available to enable them to perform functions that others can perform without special aids.

There exists in the art several devices to aid the handicapped perform limited functions even though their actions are highly restricted. U.S. Pat. No. 3,379,885 by C. L. Nork illustrates one such device. But this device permits only a simple on-off function and further restricts the operator by requiring the wearing of an attachment to the operator's head.

For more complex control, such as telephone operation, there are also available voice operated controls, such as U.S. Pat. No. 3,725,602 by Hoffman and U.S. Pat. No. 3,689,708 by Nabari, but voice operated devices have the inherent difficulty of recognition of a particular speech pattern.

The present invention solves the inadequacies of these former approaches by having the entire apparatus remote from the operator and using only the operator's eye wink as a control actuator. Moreover, since the signal generated by the wink is digital rather than analogue in nature, no recognition problem exists.

SUMMARY OF THE INVENTION

The present invention uses the unique optical characteristics of the human eye to permit an individual who can control only his eyes to use them to operate a telephone. The principle can also be extended to other complex control sequences, such as machine tool or typewriter control.

The basic components of the sight operated controller include a radiation sensor, a command discriminator and a display unit. The concept of operation is based on the fact that as radiation such as light or near infra-red radiation strikes the eye, the radiation is reflected back toward the source. The commonly experienced "red-eye" effect of flash photograph with small dimension cameras is a result of this phenomenon. The eye actually yields two radiation levels, the lessor radiation being reflected from the backlighted pupil and a significantly brighter reflection coming back from the cornea of the eye. The bright pattern which is reflected permits simple optical discrimination of the eye reflection from other sources seen by the sensor.

Such a sensor is constructed of a simple small photocell which feeds its output to the circuits of the command discriminator. The well-focused radiation beam is reflected back to the sensor when the eye is merely looking in the general direction of the sensor. When such a condition is met, an electronic signal is presented to the logic circuits of the command discriminator to activate its function.

The unit produces machine commands according to the number of times in sequence the eye is winked, or according to the length of time the eye is closed. A simple time gate discriminates, as does another human being, between an involuntary blink of very short duration and a deliberate wink of decidedly longer time duration. Similar circuits time the length of a wink to determine the instruction based on the length of time of eye closure.

Upon activation of the command discriminator the display unit is also activated. The display unit displays digital information to the operator as it is sequenced through the digits available to the operator so that he may stop the sequence at the appropriate digit by winking his eye. The automatic sequencer contains provisions for cancelling a display in case of error. The final control operation, such as placing the telephone call, is accomplished automatically once the complete instructions are received by the electronic controller, such as a touch-tone telephone keyboard.

Various functions are performed automatically when the properly coded command is presented to the command discriminator which generates the appropriate command depending upon the coded wink pattern it has received from the sensor.

DETAILED DESCRIPTION OF THE INVENTION

Figure 1:
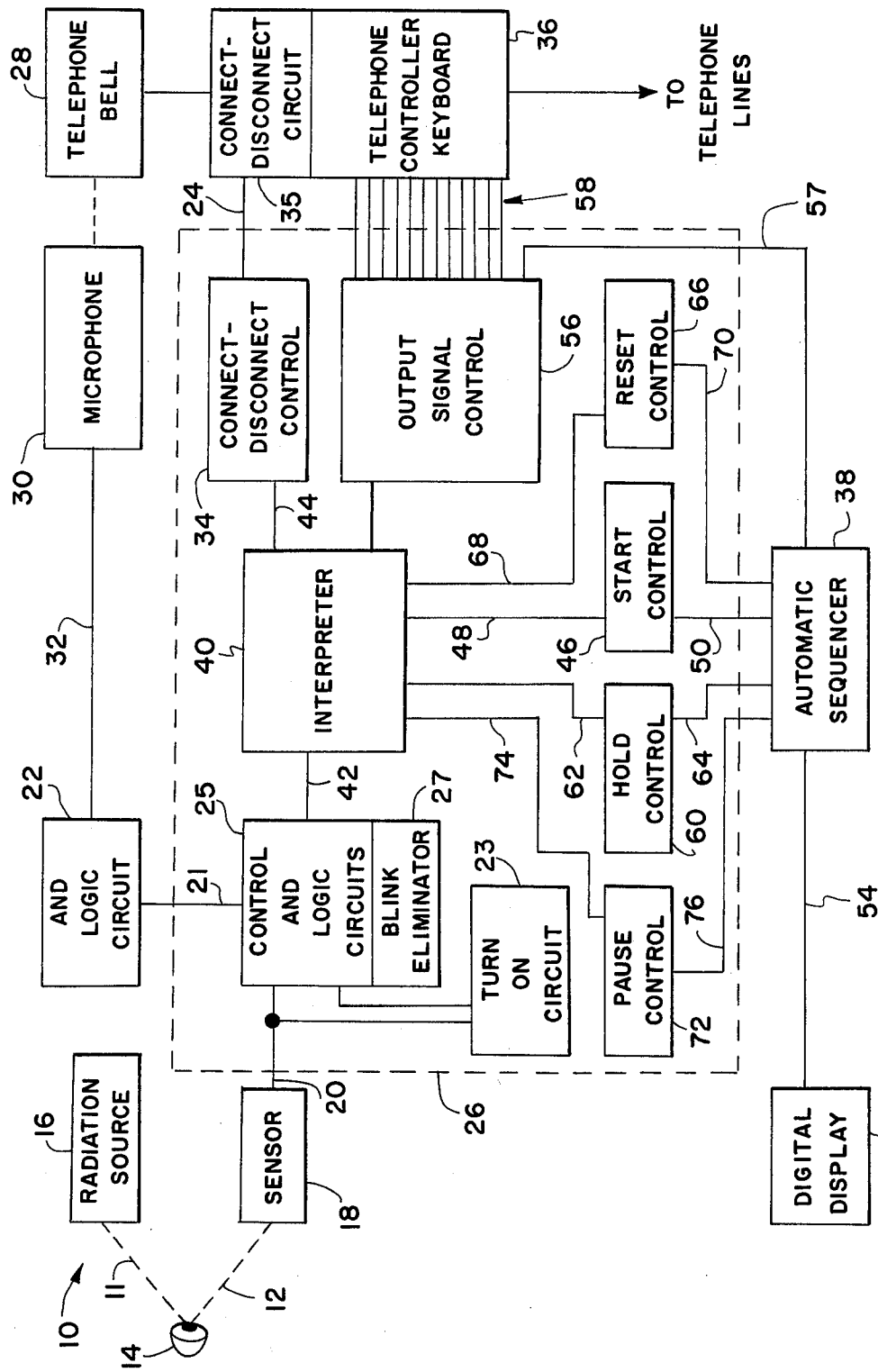
FIG. 1 is a simplified block diagram of the invention.

The basic concept and operation of the invention is illustrated in FIG. 1 which shows in block diagram form the details of a preferred embodiment related to a telephone operating control. Sight operated controller 10 acts upon the radiation beam 12 reflecting from operator's eye 14 which originates at radiation source 16. Beam 12 strikes sensor 18 to initiate the operation of sight operated controller 10. Sensor 18, consisting of a simple photosensitive element matched to the radiation of the radiation source 16, converts the reflected radiation to electrical signals and presents these signals to command discriminator 26 by means of signal path 20. The location of radiation source 16 and sensor 18 need not be exactly coaxial for the proper reflection to result, but they should not be separated by a distance which causes too great an angle of reflection. Satisfactory results can be attained for conditions in which the sight-line of the eye is as much as 60 degrees angularly displaced from the line between the radiation source and the eye. Focusing lenses and selective filters included in radiation source 16 and sensor 18 assure the system will distinguish intended radiation from other sources. The electrical signal received by command discriminator 26 is characterized only by the fact that it is presented to command discriminator 26 when the operator's eye 14 is looking in the general direction of sight operated controller 10. The signal need not vary in amplitude or any other characteristic, but it is interrupted when the operator's eye 14 blinks, winks or looks away from sight operated controller 10. A continuous signal received by command discriminator 26 indicates the operator is looking at sight operated controller 10 and turns it on by action of turn-on circuit 23.

Command discriminator 26 consists of conventional logic which by means of timed gate circuits and counters distinguishes intentional eye winking of the operator from involuntary blinking and interprets the coded instructions. The involuntary blink is of such short duration that time gates within blink eliminator 27 as short as one second completely negate the effect of such actions. "AND" logic circuit 22 is used to answer the phone when telephone bell 28 rings activating microphone 30. Microphone 30 presents an electrical signal by means of signal path 32 to "AND" logic circuit 22 preceding command discriminator 26, which if signals are presented on both signal paths 20 and 21 indicating the operator is looking at sight operated controller 10 and the telephone is ringing, activates connect-disconnect control 34 to operate connect-disconnect circuit 35 for answering the incoming call.

Command discriminator 26 also contains conventional time delay circuits which turn off all the following control functions other than turn-on circuit 23 after a phone call is initiated or answered. Turn-on circuit 23 is constantly active to the extent that the initiation of a continuous signal on path 20 will activate command discriminator 26 and all following control functions.

The basic function of command discriminator 26 is to count the number of winks of the eye of the operator and to activate one of its output lines based on the number presented. Conventional control and logic circuits 25 accomplish this counting action. The code which operates the subsequent machine functions can be varied with the operator's particular application, but the basic design need not be changed.

Moreover, the code need not necessarily be that of counting winks. A minimal amount of training can permit an operator to time the length of time of a wink quite accurately. Such time duration winks can also be used to control machine functions by merely using timing circuits within command discriminator 26 rather than counting circuits. Either type of circuit is available in conventional electronic circuitry.

When command discriminator 26 receives only a signal indicating the operator is looking at controller 10, and no other signal, turn-on circuit 23 activates all the following circuit functions. Control and logic circuits 25 then count the number of interruptions of the electrical signal on signal path 20 and present the information to interpreter 40 on signal path 42. Interpreter 40 selects the action to follow based upon the information received from control and logic circuits 25. When the signal from sensor 20 is continuous and the telephone is ringing, connect-disconnect control 34 is activated via line 44 to answer the ringing telephone.

When the signal from sensor 20 is coded, for instance, interrupted by winking of the operator's eye, various other functions are performed. In the preferred embodiment shown in FIG. 1, a continuous signal of sufficient time duration on line 20 even with no bell ringing is used to activate connect-disconnect control 34 via interpreter 40 and thereby effectively "lift the telephone receiver" to anticipate placing a call. The same effect is also used to activate start control 46 via line 48. Start control 46 then starts the operation of automatic sequencer 38 via line 50. Automatic sequencer 38, in turn, controls digital display 52 via line 54 and output signal control 56 of command discriminator 26 via line 58. Digital display 56 is thus sequenced through a selection of digits. In this embodiment digits "1" through "0" and all other symbols which are found on telephone controller keyboard 36 are in the display. At the same time, output signal control 56 is sequenced via line 57 through a selection of output signal lines 58, so that the signal line of the group of lines 58, which corresponds to the digit shown on digital display 52 is always active. Thus when digital display 52 is showing the digit "8", the signal line from output signal control 56 to telephone controller keyboard 36 which will activate the digit "8" of telephone controller keyboard 36 is activated.

When the operator sees the digit he desires displayed, he winks his eye once. This code is used to activate hold control 60 via line 62 from interpreter 40, which, in turn, stops automatic sequencer 38 via line 64. This stops digital display 52 and output signal controller 56 in the status they have attained. A second single wink after the operator has verified the digit displayed then sends a signal from output signal controller 56 to telephone controller keyboard 36 via the preselected signal line and places that number into the telephone system memory. Immediately after that action interpreter 40 automatically commands reset control 66 via line 68 to reset automatic sequencer 38 back to its starting status via line 70, and immediately following that action interpreter 40 restarts automatic sequencer 38 via start control 46. The described sequence is repeated until a complete telephone number has been placed into the telephone system memory at which time the telephone system automatically places the call.

The operator may operate the disconnect feature of connect-disconnect control 34 at any time, either when a telephone conversation is complete, or in the course of placing a call, because of a discovered error, by using a two-wink code, or, in the case of a time-duration code, a code of two time units.

Other special codes can also be used for special functions. Pause control 72, receiving an input via line 74 from interpreter 40, and controlling automatic sequencer 38 via line 76, stops the sequencing upon a three wink pattern, and, upon a four wink pattern, restarts the attained status after a stop but continues the sequence from the status displayed and yields no control signal to telephone controller keyboard 36. This function permits the operator to pause in the process of placing a call or stop the digital sequencing while talking to his party.

Figure 2:
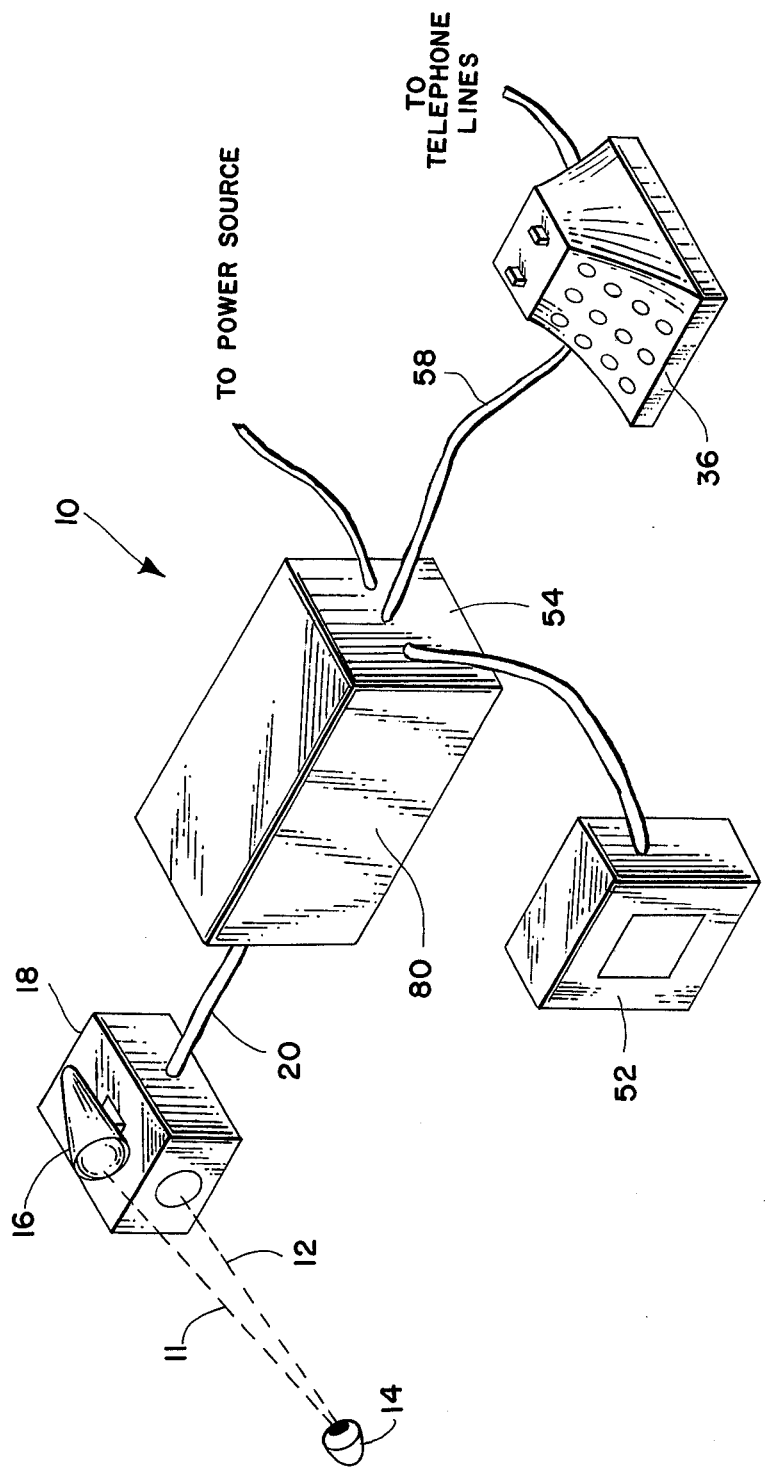
FIG. 2 is a simplified pictorial view of the invention.

FIG. 2 is a pictorial representation of the invention. Sight operated controller 10 is shown in a three cabinet configuration. Radiation source 16 radiates its energy 11 to operator's eye 14 from which it is reflected back as beam 12 to infra-red sensor 18. Signal path 20 presents the electrical signals created by sensor 18 to cabinet 80 which encloses the control circuitry of the controller other than digital display 52.

It is to be understood that the form of the invention herein shown is merely preferred embodiment. Various changes may be made in circuitry, arrangement of components, and sequence of operation; equivalent means may be substituted for those described; and certain features may be used independently from others without departing from the spirit and scope of the invention as defined in the following claims. The telephone system controlled may, for example, have substituted for it any system which may be alphabetically or numerically controlled and either normal light or infra-red radiation may be used for the radiation described above.

What is claimed as new and desired to be secured by Letters Patent of the United States is:

1. An apparatus for performing machine control functions by the use of the machine operator's eye movements comprising:

a radiation source means, aimed in the approximate direction of the operator's eye;

a radiation sensor means, placed in proximity to the radiation source means, activated by radiation reflected from the operator's eye, and producing an electrical signal dependent upon the existence of reflections from the operator's eye;

a command discriminator means electrically connected to and receiving an input signal from the radiation sensor means comprising:
  1. control and logic circuit means, connected to and receiving the input signal from the radiation sensor means, counting the number of interruptions of the input signal;
  2. interpreter means, connected to and receiving a signal from the control and logic circuit means, providing electrical signals to the various following sections of the command discriminator depending upon the number of interruptions counted by the control and logic circuit means;
  3. sequencer start control means connected to and receiving a signal from the interpreter means, producing a control signal and sending that signal to an automatic sequencer means to start an automatic sequencing action;
  4. sequencer hold control means connected to and receiving a signal from the interpreter means, producing a control signal and sending that signal to an automatic sequencer means to stop an automatic sequencing action and hold the status attained;
  5. sequencer reset control means connected to and receiving a signal from the interpreter means, producing a control signal and sending that signal to an automatic sequencer means to return the automatic sequencer to its starting status;
  6. connect-disconnect control means connected to and receiving a signal from the interpreter means and supplying an output signal suitable for turning on and turning off a machine controller; and
  7. output signal control means connected to and receiving a signal from the interpreter means, comprising several output signal lines, the selection of which are controlled by the signal from an automatic sequencer means whereby one output signal line is operational at any time and that output signal line corresponds to the sequence status of the automatic sequencer;

an automatic sequencer means, connected to and receiving electrical signals from the output lines of the several sequencer control means of the command discriminator means, producing an output control signal capable of sequencing the digits of a digital display means and connected to and producing a signal capable of sequencing the selection of output lines of the output signal control means of the command discriminator means;

a digital display means, connected to and receiving signals from the automatic sequencer means, comprising at least one numerical position indicator which can be sequenced through a choice of several alpha-numerical symbols; and a machine control means, connected to and receiving electrical signals from the output control means and the connect-disconnect control means of the command discriminator means, controlling complex machine functions based on the signal line upon which a signal is received.

2. An apparatus for performing machine control functions by the use of the machine operator's eye movements as in claim 1 further comprising:
a second sensor means connected to and furnishing a second control signal to the command discriminator means; and
an AND circuit means which verifys the presence of signal from both the first and second sensors and causes the command discriminator means to send a control signal out on one of its several signal output lines.

3. An apparatus for performing machine control functions by the use of the machine operator's eye movements as in claim 1 wherein the digital display means is capable of displaying the digits 0 through 9 for telephone dialing codes, and the machine control means comprises an electronic telephone controller.

4. An apparatus for performing machine control functions by the use of the machine operator's eye movements as in claim 2 wherein the second sensor means is a microphone for sensing a telephone bell.

5. An apparatus for performing machine control functions by the use of the machine operator's eye movements as in claim 1 wherein the radiation source means emits near infra-red radiation and the radiation sensor means comprises a photocell sensitive to near infra-red radiation.

6. An apparatus for performing machine control functions by the use of the machine operator's eye movements as in claim 1 wherein the command discriminator means includes a start recognition means, connected to the radiation sensor output signal and the control and logic circuit means, which measures the time duration of the signal from the radiation sensor and activates the control and logic circuit means only after a specified time duration with steady signal has been measured.

7. An apparatus for performing machine control functions by the use of the machine operator's eye movements as in claim 1 wherein the control and logic circuit means includes means for timing the length of time of interruption of signal from the radiation sensor means and wherein the interpreter means responds to length of time of the interruption of signal rather than to the number of interruptions counted.

8. An apparatus for performing machine control functions by the use of the machine operator's eye movements as in claim 1 wherein the command discriminator includes a sequencer pause control means connected to and receiving a signal from the interpreter means, producing a control signal and sending that signal to an automatic sequencer means to restart an automatic sequencing action from a status previously attained.

9. An apparatus for performing machine control functions by use of the machine operator's eye movements as in claim 1 wherein the command discriminator includes timing circuits which distinguish an involuntary blink from an intentional wink of the operator.

10. A method of performing machine control functions by the use of an operator's eye movements comprising:
aiming a radiation source in the direction of an operator's eye;

capturing the reflection of the radiation from the operator's eye with a radiation sensor sensitive to the radiation of the radiation source which generates an electrical signal dependent upon the presence or absence of reflected radiation;

counting the interruptions in the electrical signal generated by the radiation sensor;

controlling several functions of a digital display and a sequencing device for the digital display by matching the count of interruptions against a previously selected code for the control of each of the several functions; and operating a machine controller by matching a digit displayed upon the digital display at the time a particular number of interruptions is counted, to a digit representing a specific action by a controlled machine.

11. A method of performing machine control functions by the use of an operator's eye movements comprising:

aiming a radiation source in the direction of an operator's eye;

capturing the reflection of the radiation from the operator's eye with a radiation sensor sensitive to the radiation of the radiation source which generates an electrical signal dependent upon the presence or absence of reflected radiation;

measuring the duration of interruptions in the electrical signal generated by the radiation sensor;

controlling several functions of a digital display and a sequencing device for the digital display by matching the duration of interruptions against a previously selected code for the control of each of the several functions; and operating a machine controller by matching a digit displayed upon the digital display at the time a particular duration of interruption is measured, to a digit representing a specified action by a controlled machine.

* * * * *